United States Patent
Vogel et al.

(10) Patent No.: US 10,664,684 B2
(45) Date of Patent: May 26, 2020

(54) FINGERPRINT SENSOR WITH LIVENESS DETECTION

(71) Applicant: NEXT BIOMETRICS GROUP ASA, Oslo (NO)

(72) Inventors: Kolja Vogel, Munich (DE); Robert Müller, Riemerling (DE); Ondřej Konopka, Liberec (CZ); Radim Šmat, Prague (CZ)

(73) Assignee: NEXT Biometrics Group ASA, Oslo (NO)

( * ) Notice: Subject to any disclaimer, the term of this patent is extended or adjusted under 35 U.S.C. 154(b) by 0 days.

(21) Appl. No.: 15/748,943

(22) PCT Filed: Jun. 2, 2017

(86) PCT No.: PCT/IB2017/000778
§ 371 (c)(1),
(2) Date: Jan. 30, 2018

(87) PCT Pub. No.: WO2018/220415
PCT Pub. Date: Dec. 6, 2018

(65) Prior Publication Data
US 2019/0294852 A1    Sep. 26, 2019

(51) Int. Cl.
*G06K 9/00* (2006.01)
*A61B 5/1172* (2016.01)
(Continued)

(52) U.S. Cl.
CPC .......... *G06K 9/0012* (2013.01); *A61B 5/0059* (2013.01); *A61B 5/1172* (2013.01);
(Continued)

(58) Field of Classification Search
CPC . G06K 9/0012; G06K 9/0004; G06K 9/00087
See application file for complete search history.

(56) References Cited

U.S. PATENT DOCUMENTS

| | | | |
|---|---|---|---|
| 5,638,818 A * | 6/1997 | Diab | A61B 5/02427 356/41 |
| 6,091,837 A | 7/2000 | Dinh | |

(Continued)

FOREIGN PATENT DOCUMENTS

| | | |
|---|---|---|
| CN | 106716444 A | 5/2017 |
| TW | 201447624 A | 12/2014 |

(Continued)

OTHER PUBLICATIONS

Office Action and search report dated Mar. 8, 2019 in related TW Patent Appln. No. 107106062, pp. 1-7. (English translation provided, pp. 1-5.).

(Continued)

*Primary Examiner* — Utpal D Shah
(74) *Attorney, Agent, or Firm* — Perkins Coie LLP

(57) ABSTRACT

A fingerprint sensor device with built-in liveness detection capabilities includes: an area sensor disposed on a top surface of a substrate; a stiffener disposed below a bottom surface of the substrate; a printed circuit making electrical connection to the sensor disposed below the stiffener; and a light source and a photodetector. At least one of the light source and photodetector is disposed on the printed circuit below the area sensor. The stiffener includes at least one through-hole located with respect to the light source or photodetector to allow light from the light source to transmit through the stiffener towards a finger located on the area sensor or to allow light reflected from the finger to pass through the stiffener to the photodetector.

22 Claims, 13 Drawing Sheets

(51) Int. Cl.
*A61B 5/00* (2006.01)
*A61B 5/1455* (2006.01)
(52) U.S. Cl.
CPC ........ *A61B 5/14551* (2013.01); *G06K 9/0004* (2013.01); *G06K 9/00087* (2013.01)

(56) References Cited

U.S. PATENT DOCUMENTS

| | | | |
|---|---|---|---|
| 7,910,902 | B2 | 3/2011 | Dinh |
| 2007/0211926 | A1 | 9/2007 | Shinzaki et al. |
| 2008/0037001 | A1 | 2/2008 | Yokoyama et al. |
| 2014/0270416 | A1 | 9/2014 | Minteer et al. |
| 2015/0125050 | A1* | 5/2015 | Lee ............... G06K 9/0002 382/124 |
| 2015/0205992 | A1* | 7/2015 | Rowe ............... G06K 9/2018 382/124 |
| 2016/0041663 | A1* | 2/2016 | Chen ............... G06F 3/0412 345/174 |
| 2016/0314334 | A1* | 10/2016 | He ............... G06K 9/0012 |
| 2017/0220842 | A1* | 8/2017 | Thompson ............... G06F 21/81 |
| 2017/0364726 | A1* | 12/2017 | Buchan ............... G01N 29/2437 |
| 2018/0012069 | A1* | 1/2018 | Chung ............... A61B 5/1172 |
| 2018/0025199 | A1* | 1/2018 | Ryshtun ............... G06K 9/0002 382/125 |
| 2018/0218195 | A1* | 8/2018 | Sheik-Nainar ..... G06K 9/00013 |
| 2019/0026522 | A1* | 1/2019 | Wang ............... G06K 9/0004 |
| 2019/0095672 | A1* | 3/2019 | Yeke Yazdandoost ............... G06K 9/0004 |

FOREIGN PATENT DOCUMENTS

| | | |
|---|---|---|
| WO | 2016172713 A1 | 10/2016 |
| WO | 2017070711 A1 | 4/2017 |

OTHER PUBLICATIONS

Oberg, Pake, Laser-Doppler Flowmetry, Critical Reviews in Biomedical Engineering, (1990), vol. 18( v.2) pp. 125-163.

PCT International Search Report and Written Opinion dated Dec. 21, 2017 in corresponding PCT International Application No. PCT/IB2017/000778, pp. 1-11.

Hengfoss, et al., "Dynamic Liveness and Forgeries Detection of the Finger Surface on the Basis of Spectroscopy in the 400-1650 nm Region", Forensic Science International 212 (2011) pp. 61-68.

* cited by examiner

FINGERPRINT SENSOR WITH LIVENESS DETECTION

TECHNICAL FIELD

The present invention relates to fingerprint sensors.

CROSS-REFERENCE TO RELATED APPLICATION

This application is a U.S. national stage application under 35 U.S.C. § 371 of International Patent Application No. PCT/IB2017/000778, filed Jun. 2, 2017, which is incorporated herein in its entirety by reference.

BACKGROUND

Biometrics can establish proof-of-identity and to some extent proof of a user's intent to enter into a given transaction. In practical application, the usefulness of biometrics is limited by the precision of the biometric method (captured by false match and false non-match rates) and the quality of the system-level implementation.

One problem with biometric systems is that they can be spoofed, i.e., tricked into accepting something other than the genuine biometric trait. For example, a face-recognition system may be spoofed using a photo. And most fingerprint sensors can be spoofed with fake fingers made from different materials including paper print-outs, rubber, gelatin, silicone, wood glue, etc., particularly when made electrically conductive.

Fingerprint sensors employing the so-called "active thermal principle" are disclosed in U.S. Pat. Nos. 6,091,837 and 7,910,902, both to Ngoc Minh Dinh. The basic principle of the active thermal fingerprint sensor is the use of an array of PIN diodes as thermal sensors to differentiate the ridges and valleys of the human fingerprint since the heat transfer in these two areas are different. (A PIN diode is a diode with a wide, undoped intrinsic semiconductor region between a p-type semiconductor and an n-type semiconductor region. The p-type and n-type regions are typically heavily doped to form ohmic contacts). A typical problem with this kind of device is that latent prints left from a user on the sensor may be scanned and the sensor cannot determine when a real finger is touching the sensor. Liveness detection schemes, i.e., techniques for determining that a live subject is presenting a finger for fingerprint detection, can be used to combat these spoofing techniques and problems with latent prints.

Sensors are typically made by applying the sensing technology to a substrate material. This deposit is then covered with a protective coating. The area of the substrate material surrounding the active sensing area needs to be covered to protect it from the environment (e.g., electro-static-discharge, moisture). Thus, separate liveness detection sensors cannot be placed outside the sensor area.

There a several ways to characterize liveness detection techniques in fingerprint sensors. One way to characterize these techniques is to distinguish in-band methods from methods requiring dedicated liveness detection sensors. In-band methods look at the live image from the fingerprint sensor and try to distinguish features of live fingers which are difficult to replicate in spoofing targets. Static in-band methods look at features smaller than the ridge size, such as pores. Dynamic in-band methods look at how features of live images change over time: for example, the way a finger deforms when it lands on the sensor, or sweat escaping from the ridges as pressure increases. The advantage of in-band methods is that they do not require dedicated hardware. Their main disadvantage is that they are limited by the sensor's spatial and temporal resolution.

Hardware-based liveness detection methods require a dedicated sensor. There are three main methods known to the art. One known method is based on blood oxygenation measurement through pulse oximetry. The method relies on differences in relative absorption between oxygenated and de-oxygenated hemoglobin: oxygenated hemoglobin absorbs more light in the infrared spectrum while de-oxygenated hemoglobin absorbs more light in the red spectrum. Typical blood oxygen monitors work with two LEDs, one with a peak wavelength of 660 nm (red) and one with a peak wavelength near 940 nm (infrared). The ratio of transmitted infrared to red light allows for an estimation of blood oxygenation.

Another technique is based on the so-called blanching effect. The general principle is that when the finger lands on the sensor, blood recedes with increasing pressure and the finger changes in color, i.e., it gets lighter. This technique is described in Hengfoss, et al., "Dynamic Liveness and Forgeries Detection of the Finger Surface on the Basis of Spectroscopy in the 400-1650 nm Region", Forensic Science International 212 (2011) 61-68, the entirety of which is hereby incorporated by reference herein.

Another known technique is based on laser-doppler flowmetry. This technique uses the Doppler shift effect to detect the movement of blood particles.

SUMMARY OF THE INVENTION

In embodiments, of a fingerprint sensor device with built-in liveness detection capabilities, the fingerprint sensor device includes: an area sensor disposed on a top surface of a substrate; a stiffener disposed below a bottom surface of the substrate; a printed circuit making electrical connection to the sensor disposed below the stiffener; and a light source and a photodetector. At least one of the light source and photodetector is disposed on the printed circuit below the area sensor. The stiffener includes at least one through-hole located with respect to the light source or photodetector to allow light from the light source to transmit through the stiffener towards a finger located on the area sensor or to allow light reflected from the finger to pass through the stiffener to the photodetector.

In embodiments, the fingerprint area sensor device with built-in liveness detection capabilities, includes: an area sensor disposed on a top surface of a substrate, wherein the area sensor includes an integrated pressure or proximity sensor; a stiffener disposed below a bottom surface of the substrate; a flexible printed circuit making electrical connection to the sensor, the flexible printed circuit extending from the top surface of the substrate to a bottom side of the stiffener; and a light source and a photodetector disposed on the flexible printed circuit. The stiffener includes a first through-hole located with respect to the light source to allow light from the light source to transmit through the stiffener towards a finger located on the area sensor, and includes a second through-hole located with respect to the photodetector to allow light reflected from the finger to pass through the stiffener to the photodetector. A microcontroller is disposed on the flexible printed circuit and configured to obtain reflected light data upon detection of a finger on the area sensor through the integrated pressure sensor or proximity sensor for use in liveness detection analysis.

In embodiments, a method includes the steps of detecting presence of a finger on a fingerprint area sensor using a first detection threshold; upon detecting the presence of the finger using the first detection threshold, perform liveness detection measurements using a light source and a photodetector disposed below a sensing area of the fingerprint area sensor; detecting presence of the finger on the fingerprint area sensor using a second detection threshold greater than the first detection threshold; and upon detecting the presence of the finger using the second detection threshold, perform a fingerprint scan of the finger.

BRIEF DESCRIPTION OF THE DRAWINGS

The accompanying drawings illustrate preferred embodiments of the invention, as well as other information pertinent to the disclosure, in which.

DETAILED DESCRIPTION

Figure 1:
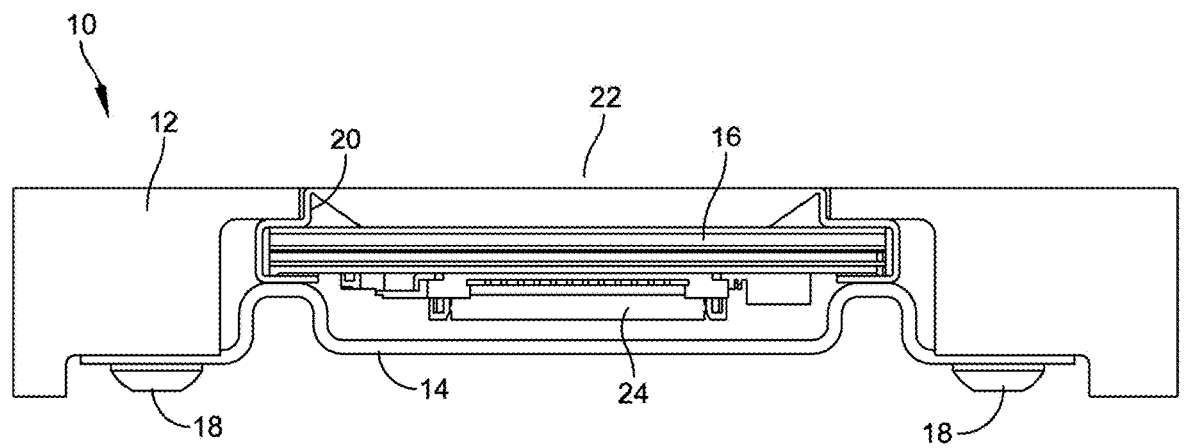
FIG. 1 is a cross-sectional view a device having a fingerprint sensor module mounted in a housing on a mounting bracket.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation, nor to be in contact with each other unless specified. Terms such as "overlap" refers to graphically cover, but not necessarily in contact with each other. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. Likewise, terms concerning electrical "connections" and "coupling" refer to a relationship wherein components communicate with one another electrically either directly or indirectly through intervening structures unless described otherwise.

In embodiments disclosed herein, a cost-effective, hardware-based, small footprint, dynamic liveness detection is realized below the sensor substrate. In embodiments disclosed herein, the liveness detection scheme is designed for fingerprint sensors employing the active thermal principle, as described in, for example, U.S. Pat. Nos. 6,091,837 and 7,910,902, both to Ngoc Minh Dinh, the entirety of which are hereby incorporated by reference herein.

The techniques described herein can be used with sensor modules that are configured to transmit an image to the host, or with embedded modules where image processing, feature extraction and matching happens on module. In the case of sensor modules, liveness can be computed on the host (for example, at the device driver level). In the case of embedded modules, liveness can be computed on the module's microcontroller, e.g., an CORTEX® M4 processor from ARM running at 166 MHz.

FIG. 1 shows a cross-section of a device 10 having a fingerprint sensor module 16 mounted in a housing 12 on a mounting bracket 14. The module 16 can be, for example, the NB-2023-S2 (SPI interface) or NB-2023-U2 (USB interface) fingerprint area sensor module available from NEXT Biometrics of Oslo, Norway. The mounting bracket 14 is coupled to the housing 12 via screws or rivets 18. The housing 12 has an opening 22. The fingerprint sensor module 16 may include a bezel 20 that serves as a finger guide. Electronics 24, such as for addressing of the sensor array, analog-to-digital conversion and/or signal processing, are coupled to the fingerprint sensor module 16. A flexible printed circuit (not shown) is bonded to the top of the sensor 16 and wraps around the side of the sensor module 16 to make contact with the mounting bracket 14, which provides a ground connection for the sensor module 16.

Figure 2:
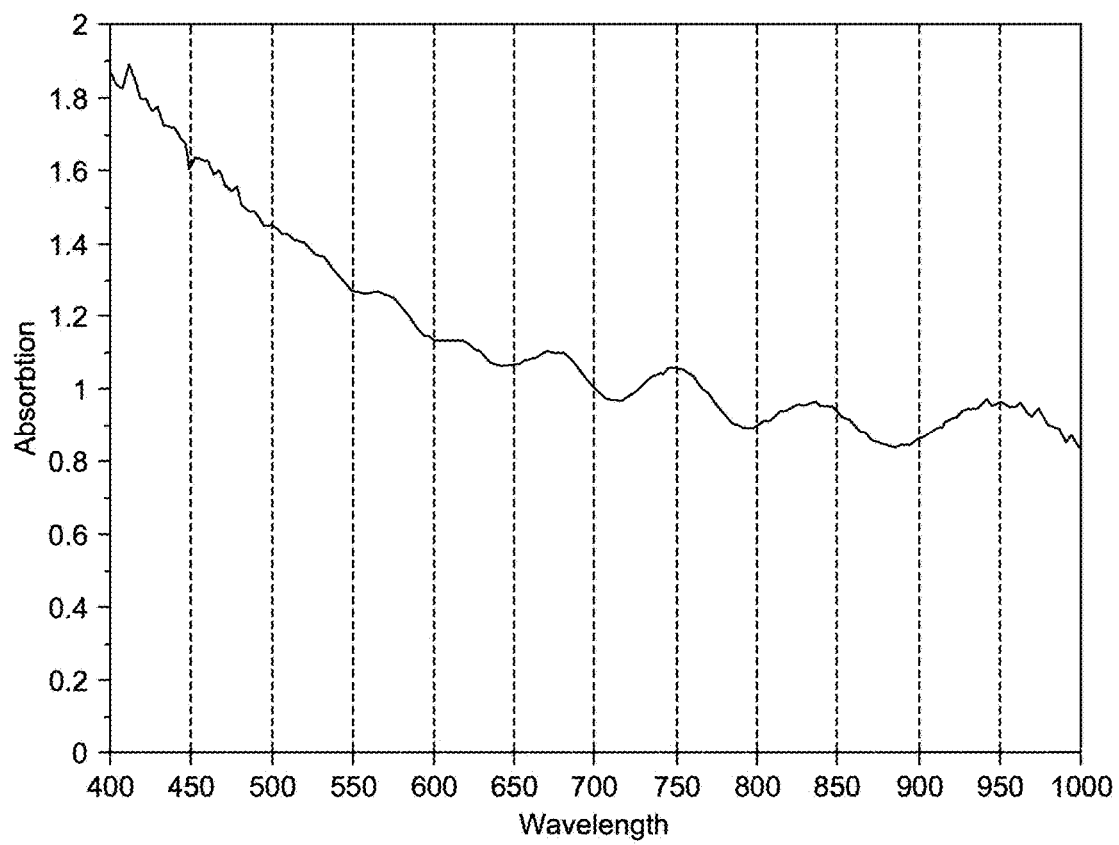
FIG. 2 shows the measured absorption spectrum in the 400 to 1000 nm range for a fingerprint sensor module.

The fingerprint sensor module 16 includes a substrate layer, which is typically glass or polyethylene; a sensing layer, such as made of low-temperature polysilicon; a protective coating layer; a stiffener that provides mechanical support for the sensing layer; and a signal processing layer, which may be a printed circuit board or flexible printed circuit with processing components thereon. These features are shown in more detail in FIG. 5 described below. The sensor technology itself and the protective coating are not transparent but also not entirely opaque. The substrate material can be chosen to be transparent, e.g. glass. FIG. 2 shows the absorption spectrum in the 400 to 1000 nm range for the NEXT Biometrics NB-S510-P2 sensor glass. The absorption scale is base 10 logarithmic, i.e. a value of 1 corresponds to $10^{-1}$ transmission (10%); a value of 2 corresponds to $10^{-2}$ transmission (1%), and so on.

Figure 3:
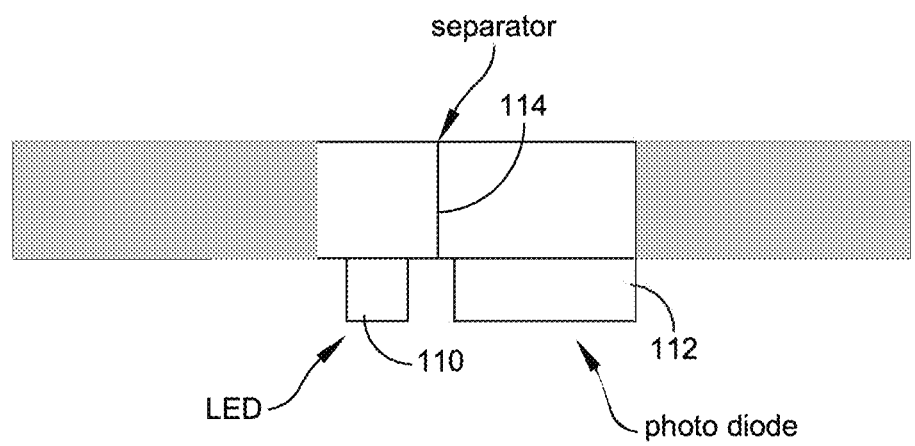
FIGS. 3 and 4 schematically illustrate side-by-side and stacked arrangements, respectively, of a light source.
Figure 4:
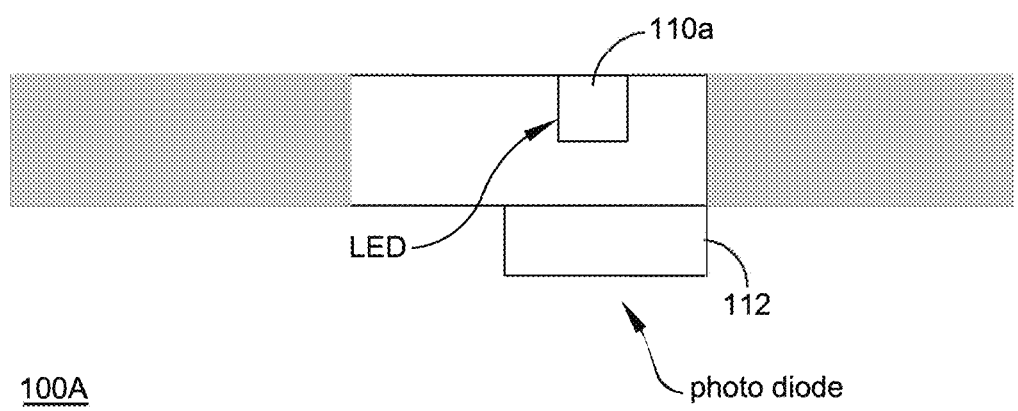

In embodiments, one or more light sources (e.g., LEDs) and zero or more photodetectors (e.g., photodiodes) may be placed underneath the sensor surface. This arrangement could be for either measuring the blanching effect or for measuring blood oxygenation (in the latter case, at least two LEDs are required). Side-by-side or stacked arrangements are possible. FIG. 3 is a schematic illustration of an embodiment of a side-by-side arrangement 100 of an LED 110 and a photodiode 112 with a separator 114 that blocks a direct light path between the two. FIG. 4 shows a stacked arrangement 100A with the LED 110a arranged above the photodiode 112 such that there is not direct light path between the LED 110a and the photodiode 112. It should be understood that the orientation of the light source (LED) and photodetector (photodiode) could be reversed, with the photodiode above the LED, as long as there is no direct light path from the LED to the photodiode.

Figure 5:
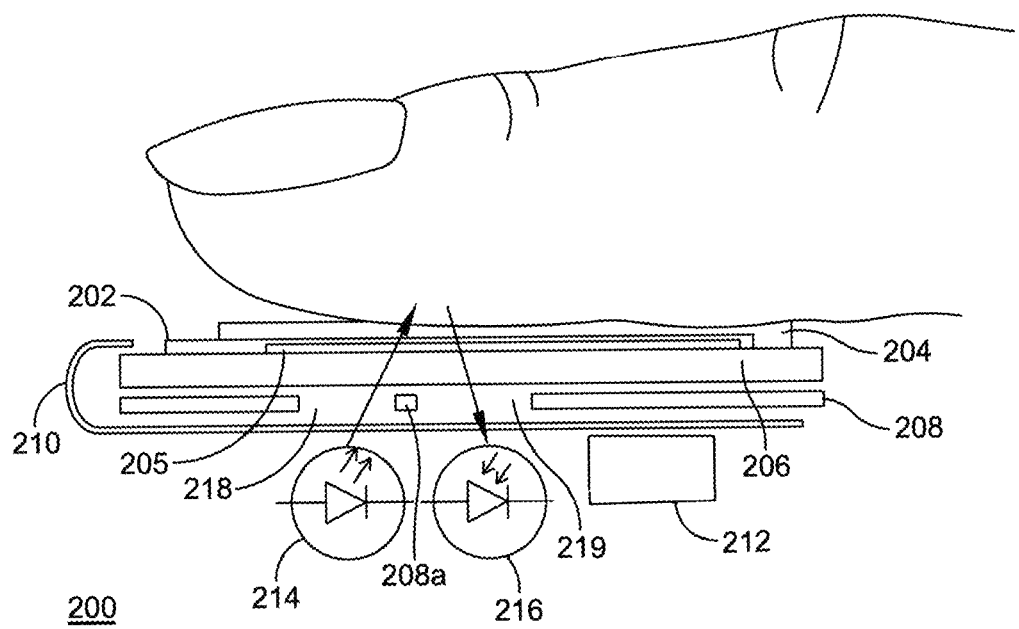
FIGS. 5 to 5F are cross-sectional views of fingerprint sensors configured for liveness detection.

It is preferred to block a direct light path between the light source (e.g., LED) and the photodetector (e.g., photodiode) so that light received by the photodetector is light that was incident on the finger. This is shown in connection with FIG. 5. FIG. 5 shows a fingerprint sensor module 200 with integrated hardware based optical liveness detection. The fingerprint sensor module 200 includes a sensor 202 (which includes an array of sensor elements in an active area 205) and a protective coating layer 204. The sensor layer 202 is formed on a substrate layer 206. A stiffener 208 is provided below the substrate layer 204. In embodiments, the stiffener 208 can be a sheet or plate of aluminum having a thickness in the range of, for example, 0.1 mm to 2 mm, and in embodiments of at least 0.2 mm. A flexible printed circuit 210 makes electrical connections between the fingerprint sensor 202 and electronics 221. Additional electronic components 212 for analog-to-digital conversion, sensor addressing and/or signal processing may be placed on the flexible printed circuit. The flexible printed circuit is used because the sensor contacts are on the finger-facing side of the module and the electronics are on the reverse side. The stiffener 208 is used to protect sensor module from bending, which offers protection to components on the flexible printed circuit 210 against mechanical damage from bending. One or more light sources 214, e.g., LEDs, and one or more photodetectors 216, e.g., photodiodes, are disposed below the stiffener 208. In addition to providing the device mechanical integrity, the stiffener 208 is configured to prevent a direct light path from light source(s) 214 to the photodetector(s) 216. In embodiments, one or more through-holes 218 are formed through the stiffener 208 above the light source(s) 214 to allow the light transmitted from the light source(s) 214 to pass through the otherwise opaque stiffener 208 to the finger. One or more through-holes 219 are also formed through the stiffener 208 to allow light reflected from the finger to be received by the photodetector(s) 216.

It should be understood that while gaps are shown between the flexible printed circuit 210, the stiffener 208 and the substrate 206, this is only for purposes of ease of illustration of these layers in the schematic illustration of FIG. 5. Any gaps between these layers should be minimized to control reflections.

Figure 5A:
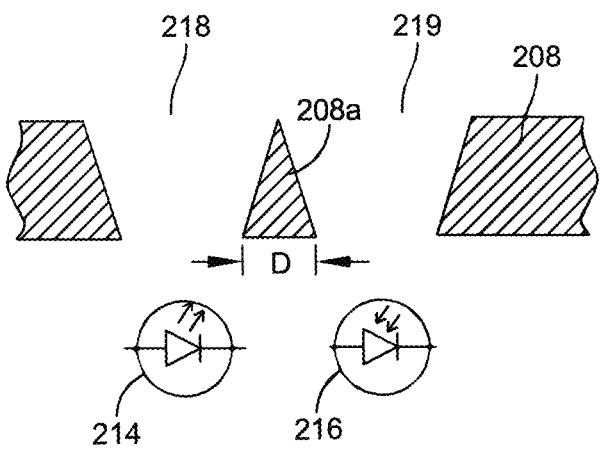

The distance between the transmitted light through-hole 218 and the reflected light through-hole 219 should be small, to maximize the amount of reflected light captured by the photodetector 216. In embodiments, the distance is in the range of 0.1 mm to 4 mm. In embodiments, the distance is less than 0.25 mm. One way to achieve a small effective distance (shown as distance D on segment 208a formed between the through-holes 218, 219) between the through holes 218, 219 without compromising mechanical stability of the stiffener, is to shape one (or both) through-holes 218, 219 as conical bores with the larger diameter facing away from the light source 214 and photodetector 216, as shown in FIG. 5A. Segment 208a serves as the separator shown in FIG. 3 that blocks any direct light path between the light source and the photodetector. In production, this can be achieved by placing two concentric bore-holes into the stiffener 208 from opposite directions. One of the bore-holes has a larger diameter and this bore hole does not travel through the entire thickness of the stiffener, thus creating a conical shape in the resulting through-hole.

Figure 5B:
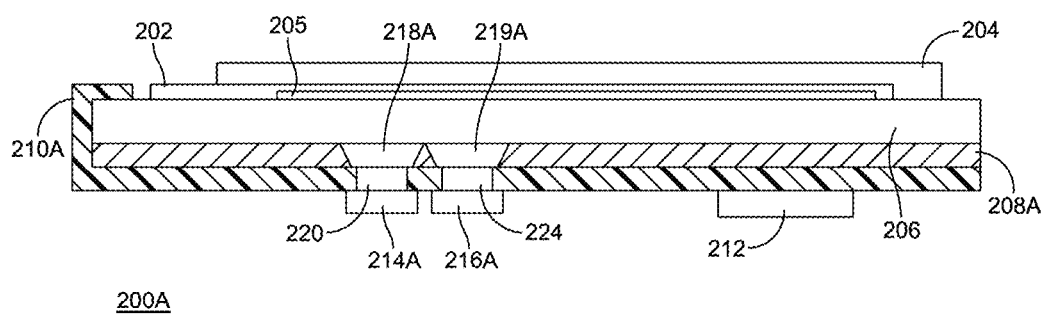
Figure 5C:
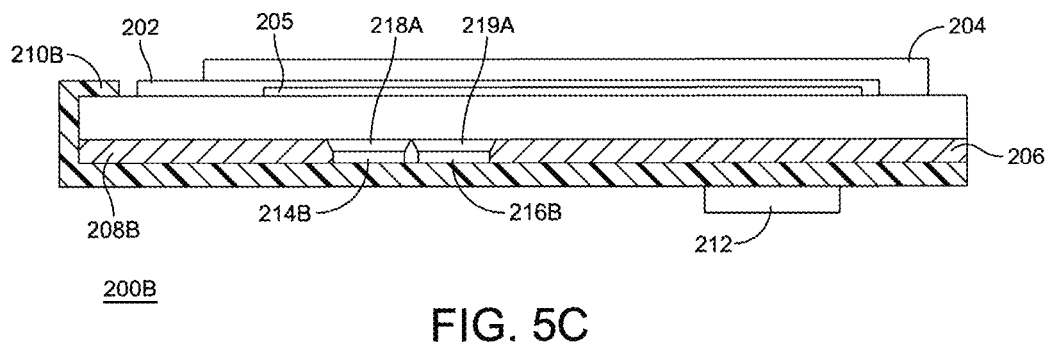

FIGS. 5B and 5C illustrate embodiments of fingerprint sensor modules 200A and 200B, respectively. Like features are labeled with like reference numerals from FIG. 5. As shown in FIG. 5B, the flexible printed circuit 210A extends from the topside of the substrate 206, where it makes electrical connections to sensor 202 through a conductive low temperature polysilicon area formed on the substrate 206 outside of the active area 205, around the side of the substrate 206 and stiffener 208A to the bottom side of the stiffener 208A. Light source 214A, photodetector 216A and one or more additional electronic components 212 (e.g., for analog-to-digital conversion and/or signal processing) are on the side of the flexible printed circuit 210A facing away from the bottom side of the stiffener 208A. Through hole 220 is formed in the flexible printed circuit 210A to align with the through hole 218A in the stiffener 208A. Through-holes 220 and 218A allow light from light source 214A to pass through the flexible printed circuit 210A and stiffener 208A towards the finger, which is placed on the sensor 202. Through hole 224 is formed in the flexible printed circuit 210A to align with the through hole 219A in the stiffener 209A. Through-holes 219A and 224 allow light reflected from the finger to pass through the stiffener 208A and the flexible printed circuit 210A to the photodetector 216A. Through holes 220 and 224 in flexible printed circuit 210A are not needed if the flexible printed circuit 210A is sufficiently translucent such that liveness detection is not impaired. Alternatively, as shown in FIG. 5C, the light source 214B and the photodetector 216B can be located on the side of the flexible printed circuit 210B that is facing the stiffener 208B. In this embodiment, the light source 214B and photodetector 216B are disposed at least partially within through holes 218B and 219B, respectively, within the stiffener 208B. In this way there is no issue with respect to the flexible printed circuit 210B interfering with light being transmitted from the light source 214B towards the finger and being received by the photodetector 216B from the finger, and the stiffener 208B blocks any direct light path between the light source 214B and photodetector 216B.

In embodiments, the through-hole 218A and through-hole 219A can be one through-hole covering both through-hole 220 and through-hole 224, assuming the flexible circuit portion separating through-hole 220 and through-hole 224 provides sufficient blocking of light emitted from the light source 214A from being received at the photodetector 216A.

In embodiments, the photodetector is placed below the light source (e.g., LED). For example, the LED and photodetectors are on different sides of the flexible printed circuit, with their active sides facing in the same direction. The component disposed on the face of the flexible printed circuit facing away from the finger would be reverse mounted. In embodiments, the light source 214B of FIG. 5C can be used with photodetector 216A of FIG. 5C. Alternatively, the light source can be placed below the photodetector. That is, light source 214A of FIG. 5B can be used with photodetector 216B of FIG. 5C. The light source and the photodetector can be laterally offset from one another or even aligned vertically with one another as long as the element on top does not block either the reflected light (in the case of the light source on top) or the transmitted light (in the case of the light source on the bottom), as the case may be, so as to adversely affect the ability to perform liveness detection analysis.

Figure 6A:
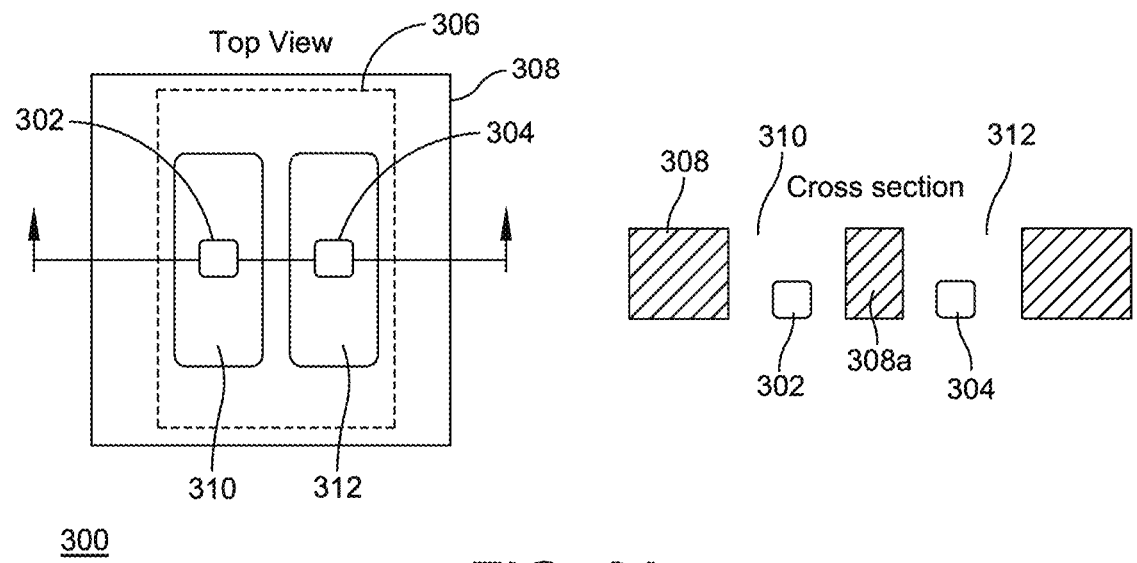
FIGS. 6A and 6B illustrate embodiments of stiffeners with through-holes for allowing transmitted light and reflected light to pass.

An embodiment of a light source/photodetector/stiffener configuration 300 is shown in FIG. 6A. FIG. 6A shows both a top view (left) and a cross-section (right). The stiffener 308 has two relatively large rectangular slots or openings formed therein, with the first opening 310 for allowing transmission of light from the light source 302 and the second opening 312 for passing reflected light to the photodetector 304. The shape of the sensor glass substrate is shown by dashed line 306. As can be seen in the cross-section, the light source 302 and photodetector 304 are received in or otherwise positioned with respect to (i.e., proximate) the openings 310, 312 so that the light path between the two is completely or substantially blocked by stiffener segment 308a (i.e., so that all or nearly all of the light received at the photodetector 304 is reflected light from the finger and not light directly from the light source 302 to the photodetector 304). The configuration 300 maximizes light emitted into the finger and light reflected from the finger and has worked well in experimental set-ups. This configuration is more susceptible, however, to ambient light being received at the photodetector due to the size of the opening 312 in the stiffener 308. Ambient light is essentially noise that decreases the systems signal-to-noise ratio (S/N).

Figure 6B:
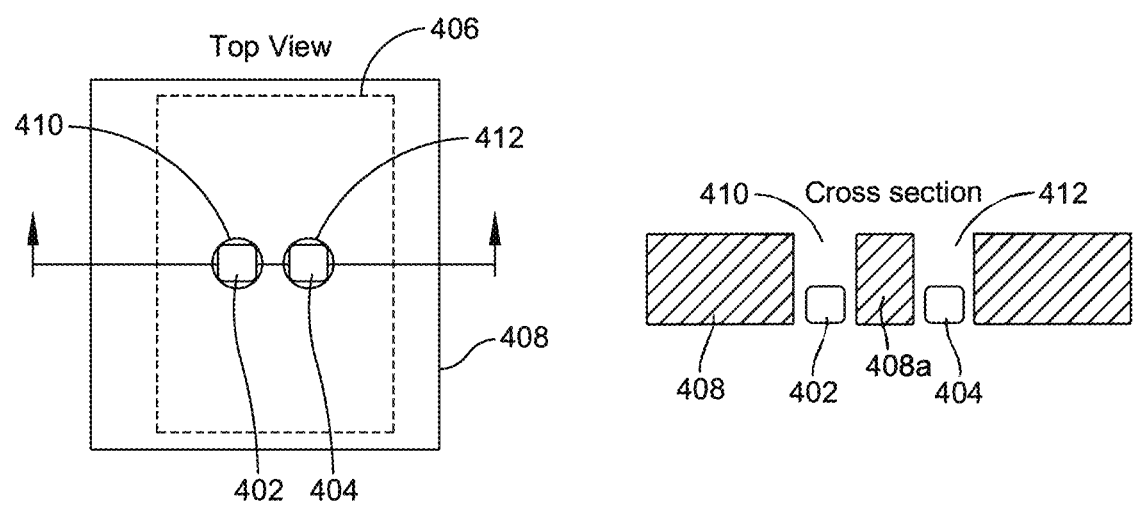

FIG. 6B illustrates an alternative embodiment of a light source/photodetector/stiffener configuration 400. FIG. 6B shows both a top view (left) and a cross-section (right). The stiffener 408 has two relatively small or narrow cylindrical slots or openings formed therein, with the first opening 410 for allowing transmission of light from the light source 402 through the stiffener 408 and the second opening 412 for allowing reflected light to pass through the stiffener 408 to the photodetector 404. The shape of the sensor glass is shown by dashed line 406. As can be seen in the cross-section, the light source 402 and photodetector 404 are received in or otherwise positioned with respect to (i.e., proximate) the openings 410, 412 so that the direct light path between the two is completely or substantially blocked by stiffener segment 408a (i.e., so that all or nearly all of the light received at the photodetector 304 is reflected light from the finger and not transmitted light from the light source 302). The configuration 400 is less sensitive to environmental ambient light, but the signal (light transmitted to the finger and reflected from the finger to the photodiode) is also weaker. It should be appreciated that the conical bore design of FIG. 5A can be used with the configurations of FIGS. 6A and 6B.

The light source/photodetector/stiffener configuration should be setup to control environmental light. Both of the configurations of FIGS. 6A and 6B prevent a direct light path between the light source and the photodetector. But the configuration of FIG. 6B is less sensitive to environmental light. However, it is also less sensitive to the signal (light from the light source reflected by the finger). The configuration of FIG. 6A in the top half of the figure illuminates the finger more evenly and allows more reflected light from the finger to reach the photodetector. However, it also admits more environmental light. In embodiments, one non-hardware approach to controlling for environmental light involves taking one or more baseline measurements with the light source (LED) OFF, and to compare them with measurements where the LED is switched ON. The difference between these measurements (or a difference of averages) is the desired signal.

It should be understood that based on this disclosure one of ordinary skill in the art can configure the shape of the holes in the stiffener, their location, size and spacing as well as the location relative thereto of the light source and photodetector so as to optimize for a given design for transmission to the finger and reception from the finger of light to the exclusion of ambient light, which is effectively noise. In embodiments, the shape and/or size of the stiffener through-hole(s) that allows for transmission of light to the finger and the shape of the stiffener through-hole(s) allow for reflected light to pass to the photodetector are different. Efforts should be made to increase the directionality of the light emitted from the light source, i.e., to provide a narrower, focused beam. If the beam's angle is too great, then too much light is dispersed within the substrate material and not enough light will be reflected from the finger. Orientation of the light source and photodetector is also important. In an experimental set up, a printed circuit board (PCB) with the light source was glued to the sensor's glass substrate. With increasing finger pressure, the substrate and PCB were bent and the detector could be fooled by placing aluminum foil over the finger. It is thus important that the stiffener is indeed "stiff". Assuming an aluminum stiffener, a thickness of 1.5 mm proved sufficient. It is possible that thinner stiffeners will also work given different materials or stiffness and through-hole configuration. In embodiments, the minimum stiffness is a stiffness sufficient to provide both mechanical protection for the device as described above while at the same time providing protection against bending that causes non-planarity (through bending) that might make the device subject to being fooled as described above. Different wavelengths for the light source were tried. An LED with peak wavelength of 570-580 nm proved best. A broad spectrum (white) LED seemed to worked better than a narrow spectrum (green) LED Experiments were performed based on liveness detection using the blanching effect. In the experiments, a temperature drift effect was observed, that could overlay the blanching effect. It was determined, therefore, that it is important to begin measurements early in the finger-placing process. A high temporal measurement resolution may help in distinguishing the temperature drift effect from the blanching effect; more than 250 Hz temporal resolution (i.e., number of measurements per unit of time) is recommended.

A preferred embodiment makes use of the blanching effect. This solution is preferred over blood oximetry and blood flow detection for two reasons. First, it is low cost. LEDs and photodiodes in the visible spectrum can be made from the cheaper Gallium phosphide (GaP), rather than the more expensive Gallium arsenide (GaAs) that is typically needed for infrared LEDs and photodiodes. Infrared LEDs and detectors are needed for blood oximetry. Surface mount device (SMD) laser elements needed for measuring the Doppler effect in blood-flow detection systems are even more expensive. Second, the blanching effect technique is fast. Measuring the dynamics of the finger landing on the sensor takes only a few hundred milliseconds. In contrast, for reliably measuring blood oxygenation, a few pulse cycles are needed (i.e., a few seconds).

As described above, one preferred embodiment places an LED and a photodiode directly adjacent to each other. However, a direct light path is prevented by a metal stiffener, placed directly in the light path. In embodiments, the stiffener has conical burrows, with the larger radii just touching (or nearly touching) each other at the top surface of the stiffener to maximize the amount of light reflected from the finger. In embodiments, the light source(s) and the photodetector(s) are placed on the flexible printed circuit within the fingerprint module. This flexible printed circuit also includes the signal processing elements for the fingerprint sensor. In embodiments, the same microcontroller used for signal processing of fingerprints is used for controlling the light source(s) and processing signals received by the photodetector(s) to do liveness detection. An analog to digital converter can be integrated into the microcontroller for converting analog signals from the photodetector to digital information. In an alternative embodiment, a dedicated analog-to-digital converter can be used. In embodiments, bit depth (i.e., number of bits available to quantify a given signal) is at least 10 bits. The light may travel through the flexible printed circuit (see FIG. 5) if the flexible printed circuit is transparent enough. Alternatively, the flexible printed circuit could have through-holes that align with those of the stiffener to allow for the light to travel freely, as shown in FIG. 5B. Alternatively, the light source and photodetector can be located on the stiffener facing side of the (flexible) printed circuit and aligned with through-holes in stiffener.

When the blanching effect principle is used, it would be advantageous in embodiments to correlate the pressure from a separate sensor (such as a capacitive sensor or piezoelectric sensor) built into the fingerprint sensor. The NEXT Biometrics fingerprint sensors identified herein have a capacitive proximity sensor (whose signal correlates to finger pressure) built-in, which could be used for the purpose. Liveness detection measurement should happen within the first few hundred milliseconds after the finger has begun to touch the sensor surface, as detected by the capacitive sensor. The Next Biometrics scanners discussed above takes about 400 milliseconds to scan a fingerprint after detection of a finger via the capacitive force sensor, which is sufficient time to accommodate liveness detection within the scan time. In embodiments, the liveness detection measurement begins when the finger touches the sensor and before the fingerprint scan begins. The fingerprint scan time and liveness detection time may overlap. With these design directives, a small, but sufficiently robust blanching effect can be observed.

The signal from the photodiode is evaluated only when the signal from a proximity or pressure sensor is in a predetermined range, preferably the capacitive sensor integrated into the fingerprint sensor.

In embodiments, a contact oil (e.g., silicone oil) with refractive index like that of the glass may be placed between light source and/or the photodetector and the surface of the substrate to minimize unwanted reflection. In embodiments, the contact oil is placed between the bottom surface of the substrate and the top surface of the stiffener.

It should be appreciated that blood oxygenation measurements could also be done through the sensor glass as a liveness detection mechanism, though it is anticipated that a longer time would be required (as compared with the blanching effect technique) for the measurement.

In embodiments, two LEDs with peak wavelength 600 nm and 940 nm, respectively, could be used to measure blood oxygenation. In embodiments, different photodetectors with different peak sensitivities and as little sensitivity overlap as possible would be provided to collect the reflected light of different wavelengths.

In embodiments, a SMD laser light source could be used, to make use of the Doppler shift effect to detect blood flow.

In embodiments, the photodetector (e.g., a photodiode) is directly integrated into the sensing layer.

Figure 5D:
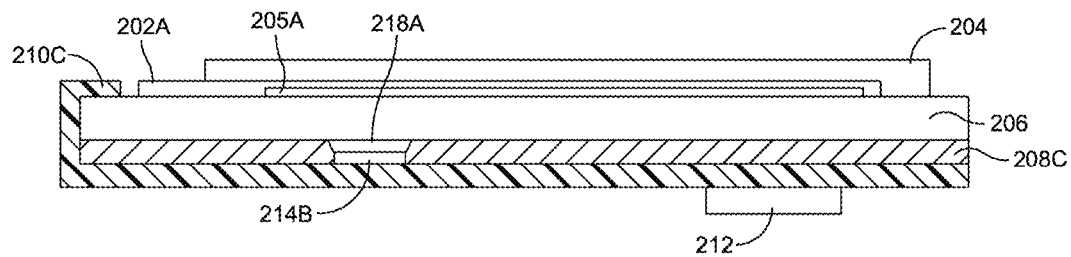
Figure 9:
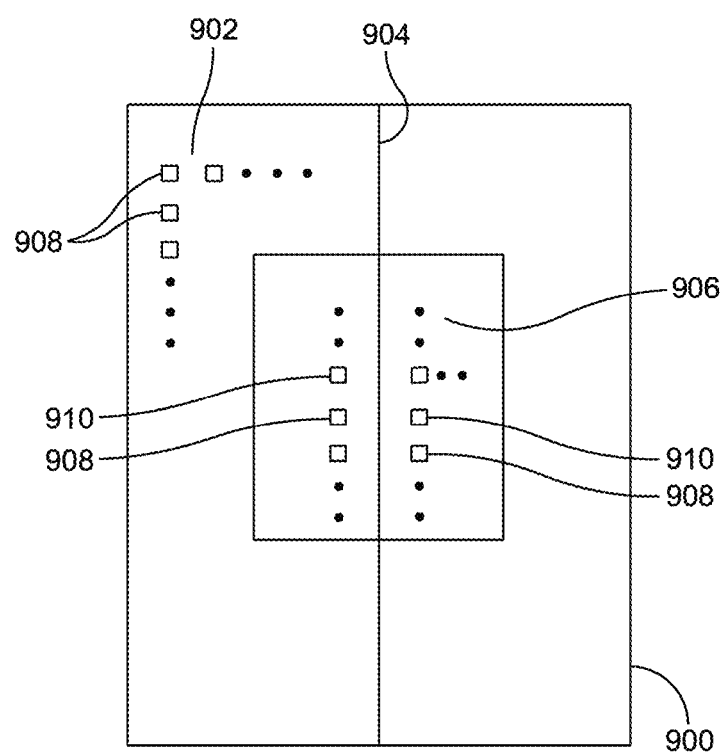
FIG. 9 shows a top view of an active area of a sensor.

FIG. 9 shows a top view of an active area 900 of a sensor. As described above, the active area 900 includes an array 902 (arranged in rows and columns) of sensor elements 908. These elements are used for capturing fingerprint image data, e.g., using the active thermal principle. A capacitive proximity sensor 904 is shown as a line going through the sensor area's center, parallel to the long edge. In embodiments, select pixels of the sensing array 902 are replaced with photodetectors 910, i.e., be dedicated to photodetection rather than thermal sensing. These pixels are ideally concentrated in the area 906 near the sensor's center. FIG. 5D shows a cross-sectional view of an embodiment of fingerprint sensor module 200C. This sensor module 200C includes a sensor 202A with an active area 205A that includes one or more photodetectors as described above in connection with FIG. 9. As such, the stiffener layer 208C only includes a through-hole 218B for passing light transmitted from the light source 214B disposed on the flexible printed circuit 210C, which does not have a photodetector disposed thereon. Connections from the photodetectors in the area 205A can be made to electronics 212 in the same manner as other connections from the sensor 202A.

Figure 5E:
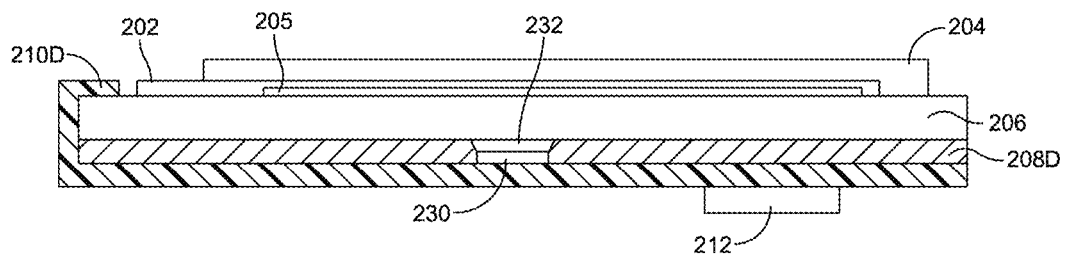

In embodiments, a single LED could be used as both the light source and photodetector, assuming sufficient sensitivity of the LED as a photodetector. An example of this embodiment is shown in FIG. 5E, which shows a cross-sectional view of an embodiment of fingerprint sensor module 200D. In this embodiment, an element 230 on the flexible printed circuit 212 serves as both light source and photodetector. Stiffener 208D includes a through-hole 232 through which both transmitted and reflected light pass.

Figure 5F:
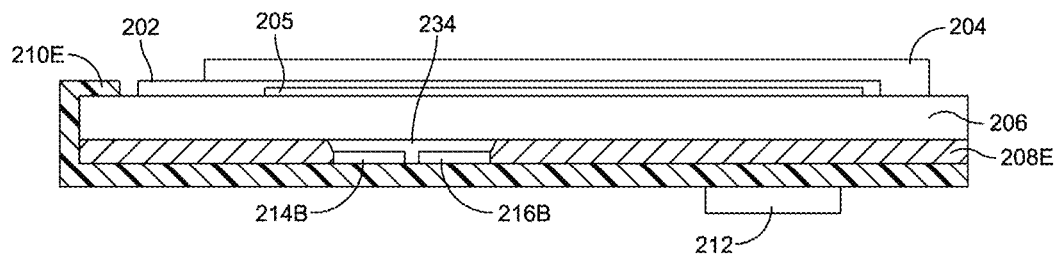

FIG. 5F is a cross-sectional view of another embodiment of fingerprint sensor module 200E. As with the embodiment of FIG. 5E, the stiffener 208E includes a through-hole 234 through which both transmitted and reflected light pass. In this embodiment, light source 214B and 216B are located adjacent to one another on flexible printed circuit 208E and within or with respect to the same through-hole 234. In this embodiment, the light source 214B can be strobed at a high rate so as to avoid emitting interfering light during detection of reflected light by the photodetector 216B. As described above, the light source and photodetector do not need to be mounted on the same side of the flexible printed circuit.

In embodiments, a dedicated proximity or pressure sensor is used to detect finger placement on the sensor and trigger liveness detection measurements.

Figure 10:
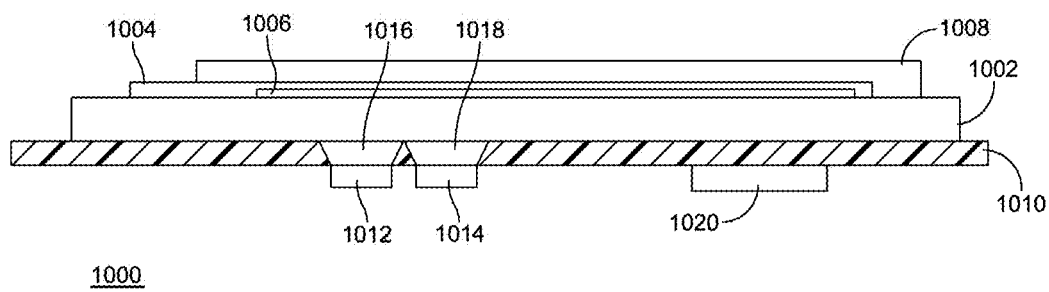
FIG. 10 shows a cross-sectional view of another embodiment of a fingerprint sensor configured for liveness detection.

Note that embodiments are describe above that use a flexible printed circuit and a separate stiffener (e.g., a thin aluminum plate). In embodiments, a rigid (non-flexible) printed circuit board assembly (PCBA) could serve the same dual function of printed circuit and stiffener. In this case, either vias or a separate flexible printed circuit (FPC) or flexible flat cable (FFC) could be used to connect the PCBA and sensor. An example of this embodiment is shown in FIG. 10. FIG. 10 shows a cross-sectional view of a fingerprint sensor module 1000. A sensor 1004 (which includes an array of sensor elements in an active area 1006) and a protective coating layer 1008 are disposed over substrate 1002. The substrate is disposed on the top surface of PCBA 1010. Electronics 1020, such as for addressing of the sensor array, analog-to-digital conversion and/or signal processing are disposed on the bottom surface of the PCBA and coupled to the sensor module 1004 as described above. Through-hole 1016 is formed through the PCBA 1010 to align with light source 1012 disposed on the bottom surface of the PCBA, and through-hole 1018 is formed through the PCBA 1010 to align with photodetector 1014 disposed on the bottom surface of the PCBA 1010. Of course, as described above, embodiments where one of the light source and photodetector are disposed on the PCBA 1010 are contemplated as well as embodiments where there is one through-hole in the PCBA 1010.

Figure 7:
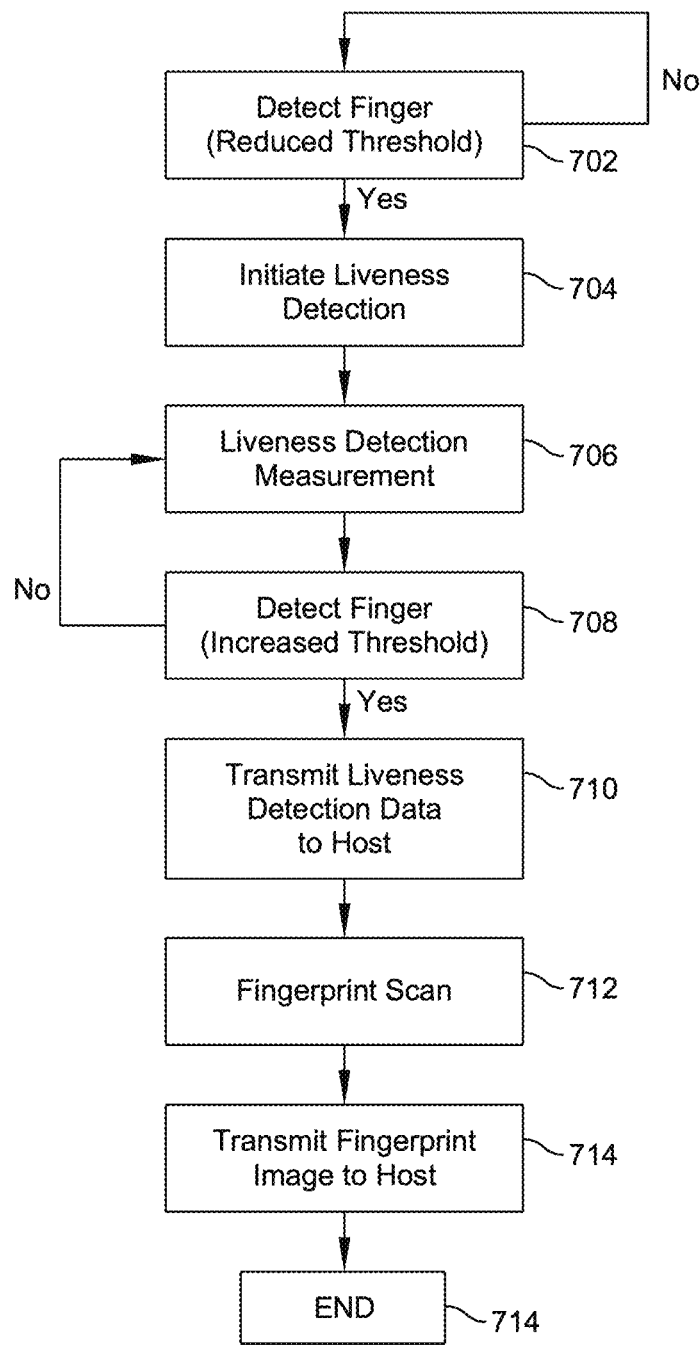
FIG. 7 is a flow diagram illustrating an embodiment of a combined liveness detection and fingerprint scanning method for a sensor module.

FIG. 7 illustrates an embodiment of a combined liveness detection and fingerprint scanning method for a sensor module that is interfaced to a host device in order for the host device to do fingerprint comparisons against stored fingerprint templates. Examples of such sensor modules include the NEXT Biometrics NB-2023-S2 and NB-2023-U2 fingerprint area sensor modules.

At 702, the presence of a finger on the sensor is detected. This step may use capacitive finger-present detection methods an use a first (reduced) threshold.

At 704, assuming the first threshold is met or exceeded, a liveness detection technique is begun. In this step the light source (LED(s)) is turned on.

At 706, dynamic liveness detection measurements are made with the photodetector(s). Several measurements are made at different finger pressures until the finger present detection at a second (increased) threshold, greater than the first threshold, (step 708) is made.

At 710, after the finger present detection at the second threshold, the measured liveness detection data is transmitted to the host device for analysis, i.e., for a determination if a "live" finger is present, e.g., using the known blanching effect.

At 712, the fingerprint scan is commenced.

At 714, the scanned fingerprint image is transmitted to the host for feature extraction and comparison with a stored template, for storage, or other use, using known techniques.

At 716, the method ends.

While FIG. 7 shows the liveness detection measurements ending with the detection of the finger at the increased threshold (step 708), it should be understood that in embodiments the liveness detection measurements continue and step 708 is used only as the trigger to begin the fingerprint scan and not to end the fingerprint measurements.

Figure 8:
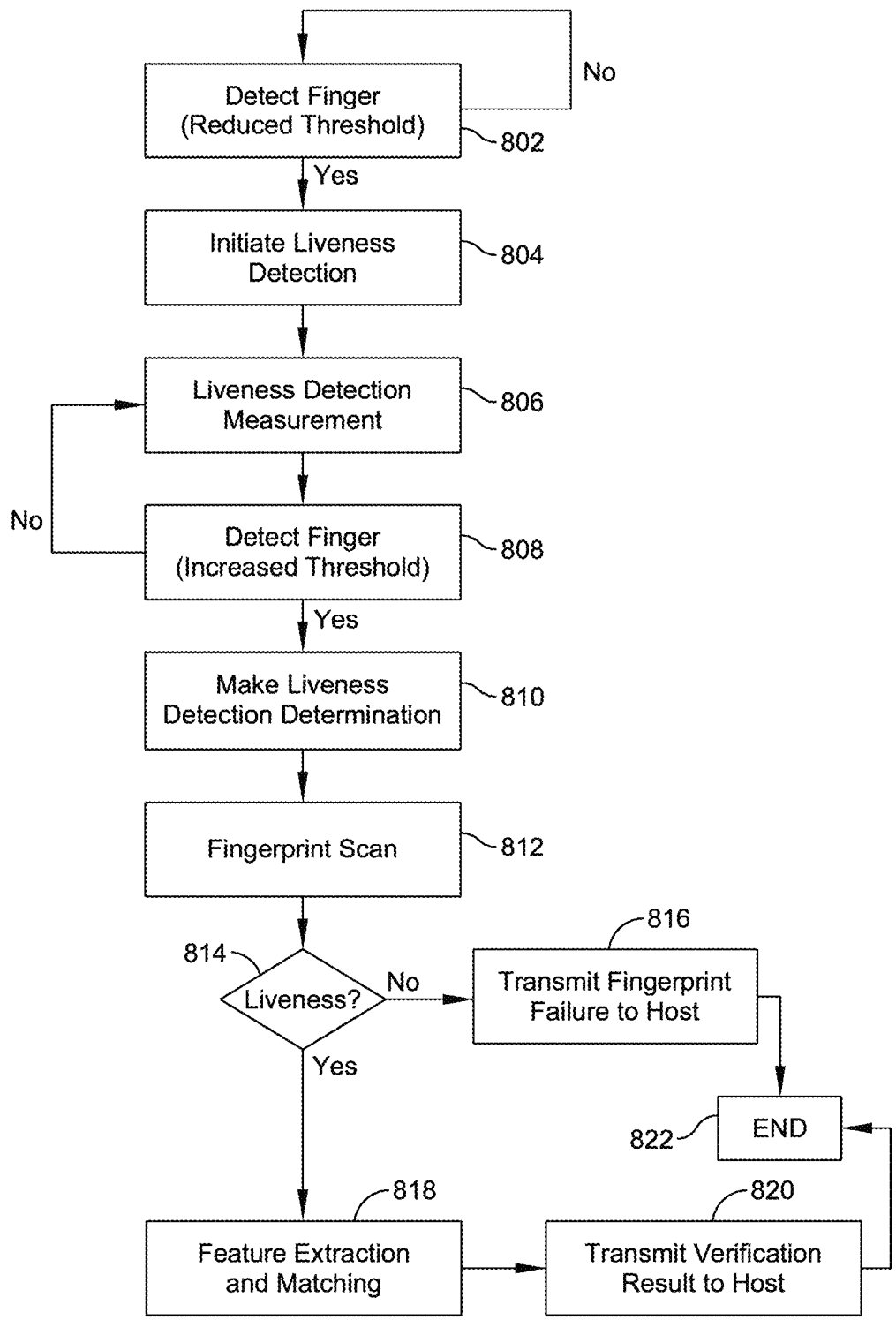
FIG. 8 is a flow diagram illustrating an embodiment of a combined liveness detection and fingerprint scanning method for an embedded sensor module.

FIG. 8 illustrates an embodiment of a combined liveness detection and fingerprint scanning method for an embedded sensor module having embedded fingerprint matching capabilities. Examples of such sensor modules include the NEXT Biometrics NB-1411-S and NB-1411-U fingerprint area embedded sensor modules. The processor that handles the fingerprint matching, or a different processor that is part of the module, is configured to perform liveness detection determinations.

At 802, the presence of a finger on the sensor is detected. This step may use capacitive finger-present detection use a first (reduced) threshold.

At 804, assuming the first threshold is met or exceeded, a liveness detection technique is begun. In this step the light source (LED(s)) is turned on.

At 806, dynamic liveness detection measurements are made with the photodetector(s). Several measurements are made at different finger pressures until the finger present detection at a second (increased) threshold, greater than the first threshold, (step 808) is made.

At 810, after the finger present detection as the second threshold, a liveness detection determination is made without transmitting the liveness detection data to a host device for analysis. The determination is based on, for example, the blanching effect.

In embodiments, at the same time the liveness detection result is being calculated, at 812, the fingerprint scan is commenced. In embodiments, the processor that handles image processing and matching (step 818) is idle during the scan operation, meaning it is free to handle liveness detection processing before being taxed by the image processing and matching operations.

At 814, it is determined if the liveness detection calculation indicated a live finger or not. If no live finger, then a failure (e.g., in the form of an authentication failure code) is sent to the host (step 816). At step 818, if the liveness detection indicated a live finger, then feature extraction and matching is performed. The result of step 818, e.g., either a positive authentication code or a negative authentication code, is transmitted to the host at step 820. The method ends at step 822.

Although the invention has been described in terms of exemplary embodiments, it is not limited thereto. Rather, the appended claims should be construed broadly to include other variants and embodiments of the invention that may be made by those skilled in the art without departing from the scope and range of equivalents of the invention.

What is claimed is:

1. A fingerprint area sensor device with built-in liveness detection capabilities, comprising:
    an area sensor disposed on a top surface of a substrate, wherein the area sensor is configured for finger-present detection;
    a stiffener disposed below a bottom surface of the substrate;
    a printed circuit making electrical connection to the sensor disposed below the stiffener;
    a light source;
    a photodetector; and
    a microcontroller disposed on the printed circuit and configured to obtain data upon detection of a finger on the area sensor for use in liveness detection analysis, and wherein the microcontroller is configured to obtain data for liveness detection upon detection of a finger on the sensor using a first sensor threshold, and is further configured to initiate scanning of the finger upon detection of a finger on the sensor using a second sensor threshold,
    wherein at least one of the light source and photodetector is disposed on the printed circuit below the area sensor;
    wherein the stiffener includes at least one through-hole located with respect to the light source or photodetector to allow light from the light source to transmit through the stiffener towards a finger located on the area sensor or to allow light reflected from the finger to pass through the stiffener to the photodetector.

2. The fingerprint area sensor device of claim 1, wherein printed circuit and stiffener are part of a rigid printed circuit board assembly, and the light source or photodetector that is disposed on the printed circuit is reverse mounted on the printed circuit board assembly.

3. The fingerprint area sensor device of claim 1, wherein the stiffener blocks a direct light path between the light source and the photodetector.

4. The fingerprint area sensor device of claim 3, wherein the stiffener includes first and second through-holes located with respect to the light source and photodetector, respectively, the first and second through-holes being adjacent to one another and a segment of the stiffener disposed between the first and second through-holes blocks the direct light path.

5. The fingerprint area sensor device of claim 1, wherein the printed circuit is part of a flexible printed circuit extending from a top surface of the substrate to a bottom side of the stiffener, wherein the flexible printed circuit has a first side facing the stiffener and a second side opposite the first side, wherein the light source and photodetector are disposed on the second side of the flexible printed circuit.

6. The fingerprint area sensor device of claim 5, wherein the flexible printed circuit is translucent to the light from the light source.

7. The fingerprint area sensor device of claim 5,
    wherein the stiffener includes first and second through-holes located with respect to the light source and photodetector, respectively, wherein the printed circuit includes a first through-hole aligned with respect to the first through-hole of the stiffener and the light source, and wherein the printed circuit includes a second through-hole aligned with respect to the second through-hole of the stiffener and the photodetector.

8. The fingerprint area sensor device of claim 1, wherein the light source or photodetector that is disposed on the printed circuit is disposed least partially within the through-hole.

9. The fingerprint area sensor device of claim 1, wherein the fingerprint area sensor device includes an analog-to-digital converter coupled to the photodetector and is configured to transmit data corresponding to light detected by the photodetector to a host device for liveness detection analysis.

10. The fingerprint area sensor device of claim 1, further comprising a microcontroller coupled to the photodetector for performing liveness detection analysis based on light detected by the photodetector.

11. The fingerprint area sensor device of claim 10, wherein the microcontroller is further configured to perform fingerprint matching analysis.

12. The fingerprint area sensor device of claim 1, wherein the stiffener comprises a sheet of aluminum and the printed circuit is part of a flexible printed circuit.

13. The fingerprint area sensor device of claim 1, wherein the photodetector is formed within the area sensor and the light source is disposed on the printed circuit below the area sensor.

14. The fingerprint area sensor device of claim 1, wherein the light source and photodetector are provided by one integral device disposed on the printed circuit below the area sensor.

15. A fingerprint area sensor device with built-in liveness detection capabilities, comprising:
an area sensor disposed on a top surface of a substrate;
a stiffener disposed below a bottom surface of the substrate;
a printed circuit making electrical connection to the sensor disposed below the stiffener;
a light source;
a photodetector;
wherein at least one of the light source and photodetector is disposed on the printed circuit below the area sensor;
wherein the printed circuit and stiffener are part of a rigid printed circuit board assembly, and the light source or photodetector that is disposed on the printed circuit is reverse mounted on the printed circuit board assembly;
wherein the stiffener includes first and second through-holes located with respect to the light source and photodetector, respectively, the first and second through-holes being adjacent to one another and a segment of the stiffener disposed between the first and second through-holes blocks a direct light path between the light source and the photodetector; and
wherein walls of the first and second through-holes are sloped towards the light source and photodetector, respectively.

16. A fingerprint area sensor device with built-in liveness detection capabilities, comprising:
an area sensor disposed on a top surface of a substrate, wherein the area sensor includes an integrated pressure or proximity sensor;
a stiffener disposed below a bottom surface of the substrate;
a flexible printed circuit making electrical connection to the sensor, the flexible printed circuit extending from the top surface of the substrate to a bottom side of the stiffener;
a light source and a photodetector disposed on the flexible printed circuit;
wherein the stiffener includes a first through-hole located with respect to the light source to allow light from the light source to transmit through the stiffener towards a finger located on the area sensor;
wherein the stiffener includes a second through-hole located with respect to the photodetector to allow light reflected from the finger to pass through the stiffener to the photodetector;
a microcontroller disposed on the flexible printed circuit and configured to obtain reflected light data upon detection of a finger on the area sensor through the integrated pressure or proximity sensor for use in liveness detection analysis; and
wherein the microcontroller is configured to obtain the reflected light data upon detection of the finger on the area sensor using a first threshold, and is further configured to initiate scanning of the finger upon detection of the finger on the area sensor using a second threshold, wherein the second threshold is higher than the first threshold.

17. The fingerprint area sensor device of claim 16, wherein the reflected light data is for use in liveness detection analysis based on a blanching effect.

18. The fingerprint area sensor device of claim 17, wherein the light from the light source has a wavelength in the range of 570-580 nm.

19. A method comprising the steps of:
detecting presence of a finger on a fingerprint area sensor using a first detection threshold;
upon detecting the presence of the finger using the first detection threshold, perform liveness detection measurements using a light source and a photodetector disposed below a sensing area of the fingerprint area sensor;
detecting presence of the finger on the fingerprint area sensor using a second detection threshold greater than the first detection threshold; and
upon detecting the presence of the finger using the second detection threshold, perform a fingerprint scan of the finger.

20. The method of claim 19, further comprising the steps of:
transmitting liveness detection measurement data to a host for liveness detection analysis; and
transmit and fingerprint scan data to the host for fingerprint matching analysis.

21. The method of claim 19, further comprising steps of:
making a liveness detection determination and transmitting an indication of the determination to a host;
performing a fingerprint matching analysis and transmitting a verification result to the host.

22. The method of claim 19, further comprising the step of performing liveness detection using a blanching effect.

* * * * *